(12) United States Patent
Collin

(10) Patent No.: US 6,491,931 B1
(45) Date of Patent: *Dec. 10, 2002

(54) COSMETIC COMPOSITION COMPRISING FIBERS AND A FILM FORMING POLYMER

(75) Inventor: Nathalie Collin, Sceaux (FR)

(73) Assignee: L'Oréal S.A.

( * ) Notice: Subject to any disclaimer, the term of this patent is extended or adjusted under 35 U.S.C. 154(b) by 0 days.

This patent is subject to a terminal disclaimer.

(21) Appl. No.: 09/612,230

(22) Filed: Jul. 7, 2000

(30) Foreign Application Priority Data

Jul. 8, 1999 (FR) .............................. 99 08959

(51) Int. Cl.⁷ .............................. A61K 6/00; A61K 7/06; A61K 7/04; A61K 7/021
(52) U.S. Cl. ........................ 424/401; 424/61; 424/63; 424/70.7
(58) Field of Search .............................. 424/401, 70.7, 424/63, 61

(56) References Cited

U.S. PATENT DOCUMENTS

| | | | |
|---|---|---|---|
| 4,659,562 A | | 4/1987 | Arraudeau et al. |
| 5,858,338 A | * | 1/1999 | Piot et al. .................. 424/70.7 |
| 5,874,072 A | * | 2/1999 | Alwattari et al. ........... 424/70.7 |
| 5,876,704 A | * | 3/1999 | Collin et al. .................... 424/63 |
| 5,965,146 A | * | 10/1999 | Franzke et al. .............. 424/401 |
| 5,972,502 A | * | 10/1999 | Jessee et al. ................. 428/370 |
| 6,001,338 A | * | 12/1999 | Mondet ........................ 424/61 |
| 6,106,813 A | * | 8/2000 | Mondet et al. ................ 424/61 |
| 6,342,237 B1 | | 1/2002 | Bara .......................... 424/401 |

FOREIGN PATENT DOCUMENTS

| | | | |
|---|---|---|---|
| EP | 0 637 600 | * | 2/1995 |
| EP | 0 847 752 | | 6/1998 |
| JP | 57-158714 | | 9/1982 |
| JP | 3-153613 | | 7/1991 |
| JP | 9-263518 | | 10/1997 |
| WO | WO 97/29734 | | 8/1997 |

OTHER PUBLICATIONS

Derwent Abstract of EP 0 637 600; Derwent acc. No. 1995–068424, 1995.*
Bertrand Piot and Nathalie Collin, Co–pending U. S. patent application No. 09/984,184, "Cosmetic Composition Comprising at Least One Fiber and at Least One Wax," filed Oct. 29, 2001.
Patent Abstracts of Japan, vol. 012, No. 110, Apr. 8, 1988, JP 62 238211.
English language Derwent Abstract of EP 0 847 752, 1998.
English language Derwent Abstract of JP 57–158714, 1982.
English language Derwent Abstract of JP 3–153613, 1991.
English language Derwent Abstract of JP 9–263518, 1987.

* cited by examiner

*Primary Examiner*—Michael G. Hartley
*Assistant Examiner*—Michael A. Willis
(74) *Attorney, Agent, or Firm*—Finnegan, Henderson, Farabow, Garrett & Dunner, L.L.P.

(57) ABSTRACT

A process for making up or caring for keratin fibers. A composition comprising at least one film-forming polymer in the form of particles in aqueous dispersion, wherein the at least one film-forming polymer is chosen from polyurethanes, and fibers is applied to the keratin fibers. A cosmetic composition comprising at least one film-forming polymer in the form of particles in aqueous dispersion, wherein the at least one film-forming polymer is chosen from polyurethanes, at least one wax, and fibers, can also be applied to the keratin fibers.

73 Claims, No Drawings

COSMETIC COMPOSITION COMPRISING FIBERS AND A FILM FORMING POLYMER

The present invention relates to a process for making up or caring for keratinous fibers, comprising applying to the fibers a composition comprising fibers and an aqueous dispersion of at least one film forming polymer. The invention also relates to a make-up or care composition for keratin fibers, wherein the composition comprises fibers, an aqueous dispersion of at least one film forming polymer, and at least one wax. Specifically, the invention relates to the use of this composition for making up substantially longilinear keratin fibres of human beings, such as eyelashes, eyebrows, and hair, as well as for artificial eyelashes and wigs. More specifically, the invention relates to a mascara composition.

It is known, for example in document JP-A-3 153 613, the disclosure of which is specifically incorporated by reference herein, to use fibers in mascara compositions in order to give a lengthening and thickening effect to the eyelashes. Documents JP-A-57 158 714 and JP-9-263 518, the disclosures of which are specifically incorporated by reference herein, describe mascara compositions comprising fibers and polymers in aqueous dispersion of acrylic type. However, the make-up composition obtained is not resistant to water, such as, for example, during bathing or when taking showers, and is not resistant to tears and/or to perspiration. The make-up compositions thus do not have good staying power over time.

An aim of the present invention, therefore, is to propose a make-up composition for keratin fibers, such as the eyelashes, which has at least one of the following properties: good staying power over time, resistance to water, in particular while rubbing, and, at the same time, imparts good lengthening properties to the eyelashes.

The inventors have discovered, surprisingly, that the use of a polyurethane dispersion combined with fibers makes it possible to make an aqueous composition water-resistant, whereas previously, so-called "waterproof" mascaras were anhydrous compositions. Further, at least some embodiments of the make-up composition according to the invention have good cosmetic properties, adhere well to the eyelashes and coat them without forming blobs. In addition to being water-resistant, the make-up composition of at least some embodiments does not "crumble" by the end of the day.

Thus, a subject of the invention is a process for making up or caring for keratin fibers, comprising applying to the keratin fibers a composition comprising, in a physiologically acceptable medium, fibers and at least one film-forming polymer in the form of particles in aqueous dispersion, wherein the film-forming polymer is a polyurethane. Another subject of the invention is a cosmetic composition comprising, in a physiologically acceptable medium, fibers, at least one film-forming polymer in the form of particles in aqueous dispersion, and at least one wax, wherein the film-forming polymer is a polyurethane. Another subject of the invention is a process for forming at least one film of fibers and a polyurethane polymer in the form of particles in aqueous dispersion on keratin fibers, comprising applying to the keratin fibers a make-up or care composition according to the invention, wherein the film is transfer-resistant to at least one of water, tears, and perspiration when the keratin fibers are exposed thereto.

The fibers which can be used in the composition of the invention can be fibers of synthetic, natural, mineral, and organic origin. They can be short or long, hollow or solid, individual or organized, such as, for example, like plaits or braids, and any combination thereof. They can be in any shape, and, for example, of circular or polygonal cross section, such as square, hexagonal, or octagonal, depending on the specific application envisaged. Further, their ends can be blunt and/or smooth to prevent injury.

The fibers can generally have a length, in one embodiment, ranging from 0.1 mm to 10 mm, in another embodiment ranging from 1 mm to 5 mm, and in another embodiment ranging from 1 mm to 3.5 mm. Their cross section can be included in a circle of diameter ranging from 500 nm to 500 $\mu$m in one embodiment, in another embodiment in a circle of diameter ranging from 10 nm to 100 $\mu$m, and in another embodiment in a circle of diameter ranging from ranging from 20 $\mu$m to 50 $\mu$m. The weight of the fibers is often given in denier or decitex.

The fibers which can be used according to the invention can be those used in the manufacture of textiles, such as, for example, silk fibers, cotton fibers, wool fibers, or flax fibers, cellulose fibers (or Rayon), such as, for example, extracted fibers such as fibers from wood, plants, or algae, polyamide (Nylon®) fibers, viscose fibers, acetate fibers, such as, for example, rayon acetate fibers, poly(p-phenyleneterephthalamide) (or aramide) fibers, such as, for example, Kevlar®, acrylic polymer fibers, such as, for example, polymethyl methacrylate or poly(2-hydroxyethyl methacrylate) fibers, polyolefin fibers, such as, for example, polyethylene or polypropylene fibers, silica fibers, carbon fibers, such as, for example, in graphite form, polytetrafluoroethylene fibers (such as Teflon®), insoluble collagen fibers, polyester fibers, polyvinyl chloride fibers, polyvinylidene chloride fibers, polyvinyl alcohol fibers, polyacrylonitrile fibers, chitosan fibers, polyurethane fibers, polyethylene phthalate fibers, fibers formed from a mixture of polymers such as those mentioned above, such as, for example, polyamide/polyester fibers, and mixtures of different fibers.

Moreover, the fibers can be surface-treated or untreated, and can be coated or uncoated. Coated fibers which can be useful according to the invention can be, for example, polyamide fibers coated with copper sulphide for an anti-static effect, such as, for example R-STAT from Rhodia, or fibers coated with another polymer to facilitate the specific organization of the fibers (specific surface treatment), or fibers with a surface treatment which induces color and/or hologram effects, such as, for example, Lurex fiber from Sildorex.

In one embodiment, fibers of synthetic origin can be used, for example, organic fibers, such as those used in surgery. For example, water-insoluble fibers can be used. The fibers which can be used according to the invention are generally polyamide or cellulose fibers. They can generally range in length, in one embodiment, from 0.1 mm to 5 mm, and in another embodiment from 0.25 mm to 1.6 mm, and their average diameter can generally range from 5 $\mu$m to 50 $\mu$m. For example, the polyamide fibers sold by the company P. Bonte under the name Polyamide 0.9 Dtex 0.3 mm, having an average diameter of 6 $\mu$m, a weight of about 0.9 decitex, and a length ranging from 0.3 mm to 1.5 mm, can be used. Poly-p-phenylene terephthalamide fibers with an average diameter of 12 $\mu$m and a length of about 1.5 mm can also be used, such as those sold under the name Kevlar Floc by the company DuPont Fibers. Cellulose (or Rayon) fibers having an average diameter of 50 $\mu$m and a length ranging from 0.5 mm to 6 mm, such as those sold under the name Natural rayon flock fiber RC1BE-N003-M04 by the company Claremont Flock can also be used. Polyethylene fibers can also be used, such as those sold under the name Shurt Stuff 13 099 F by the company Mini Fibers.

The fibers can be present in the composition according to the invention, in one embodiment, in an amount generally ranging from 0.1% to 10% by weight, relative to the total weight of the composition, and in another embodiment from 0.3% to 5% by weight.

In the present application, the expression "film-forming polymer" means a polymer which is capable, by itself or in the presence of a film-forming auxiliary agent, of forming an isolable film. The expression "polymer in the form of particles in aqueous dispersion," generally known as a latex or pseudolatex, means a phase containing water and, optionally, a compound which is soluble in water, in which the polymer is dispersed directly in the form of particles.

The polyurethane used according to the invention can be chosen, for example, from polyester-polyurethanes and polyether-polyurethanes. The polyurethane can, for example, be an anionic polyurethane, and can be chosen from polyurethanes capable of forming a film which has a hardness ranging from 10 seconds to 200 seconds. The hardness of the polymer film is measured on film obtained after drying a coat which was 300 μm thick (before drying) of an aqueous dispersion containing 28% solids of the said radical-mediated polymer particles for 24 hours at 30° C. and at 50% relative humidity. The hardness of the film is measured according to ASTM standard D-43-66, or standard NF-T 30-016 (October 1981), using a Persoz pendulum.

According to a first embodiment of the invention, the polyurethane can generally have a water uptake of less than or equal to 30%, and in another embodiment can have a water uptake ranging from 0.5% to 15%. The polyester-polyurethanes according to the invention can have these water uptake properties. Such polyurethanes make it possible to obtain a make-up product which, in specific embodiments, has good staying power over time and/or good water resistance. By good staying power, it is meant that the composition remains on the surface to which it is applied for a greater period of time than a composition not comprising fibers and at least one film-forming polymer in the form of particles in an aqueous dispersion. In one embodiment of the invention, polyester-polyurethanes capable of forming a film which has a hardness ranging from 40 to 200 seconds can be used, and in another embodiment, polyester-polyurethanes capable of forming a film which has a hardness ranging from 50 to 170 seconds, can be used.

According to the present application, the expression "water uptake of the polyurethane" means the percentage of water absorbed by the polyurethane after immersion for 10 minutes in water at 30° C. The water uptake is measured for a film obtained after drying a coat 300 μm thick (before drying) of an aqueous dispersion deposited on a plate for 24 hours at 30° C. and at 50% relative humidity. Pieces of the film about 1 cm² in area cut out of the dry film are weighed (mass measurement M1) and then immersed in water for 10 minutes. After immersion, the piece of film is wiped to remove the excess surface water and then weighed (mass measurement M2). The difference M2−M1 corresponds to the amount of water absorbed by the polymer. The water uptake is equal to [(M2−M1)/M1]×100, and is expressed as a percentage weight of water relative to the weight of polymer.

According to another embodiment of the invention, the polyurethane can have a water uptake of greater than 30%, a water uptake ranging from 30% to 150% in another embodiment, and a water uptake ranging from 40% to 100% in another embodiment. Use of polyether-polyurethanes according to the invention having these water uptake properties makes it possible to obtain a make-up product that adheres well to the eyelashes, and/or also has good staying power over time. Polyether-polyurethanes suitable for forming a film with a hardness ranging from 10 to 40 seconds can be used according to one embodiment of the invention, and polyether-polyurethanes suitable for forming a film with a hardness ranging from 20 to 35 seconds can be used according to another embodiment of the invention.

The polyurethane particles dispersed in the aqueous medium of the composition generally have a size ranging from 10 nm to 300 nm according to one embodiment, and ranging from 20 nm to 200 nm according to another embodiment.

Polyester-polyurethanes which can be used are, for example, those sold under the names "AVALURE UR-425," "AVALURE UR-430", "AVALURE UR-405," and "AVALURE UR 410" by the company Goodrich. Polyether-polyurethanes which can be used are, for example, those sold under the names "SANCURE 878," "AVALURE UR-450," and "SANCURE 861" by the company Goodrich.

The polyurethane can be present in the composition used in the process according to the invention, in one embodiment, in an amount generally ranging from 1% to 60% by weight of solids, relative to the total weight of the composition, can be present in an amount ranging from 2% to 25% by weight of solids in another embodiment, and can be present in an amount ranging from 2% to 10% by weight of solids in another embodiment.

The composition according to the invention can also comprise at least one wax. The wax can be chosen from waxes of animal origin, waxes of plant origin, waxes of mineral origin, synthetic waxes, and various fractions of waxes of natural origin. The waxes can be generally present in one embodiment of the invention in an amount ranging from 0.5% to 40% by weight, relative to the total weight of the composition, ranging from 2% to 40% by weight in another embodiment, ranging from 5% to 30% by weight in another embodiment, and ranging from 10% to 25% by weight in yet another embodiment.

The wax can be chosen from waxes (I) having a melting point ranging from 70° C. to 110° C. These waxes can have a needle penetration generally ranging from 1 to 7.5. The needle penetration of the waxes is determined according to French standard NF T 60-123, or US standard ASTM D 1321, at a temperature of 25° C. According to these standards, the needle penetration is a measurement of the depth, expressed in tenths of a millimeter, to which a standardized needle weighing 2.5 g mounted in an assembly weighing 97.5 g and placed on the wax to be tested, for 5 seconds, penetrates into the wax.

The waxes (I) can be chosen from, for example, rice bran wax, carnauba wax, ouricury wax, candelilla wax, montan waxes, sugar cane wax, and certain polyethylene waxes which satisfy the criteria for the waxes (I). The composition according to the invention can comprise, in one embodiment of the invention, an amount of waxes (I) generally ranging from 0.1% to 20% by weight, relative to the total weight of the composition, and an amount of waxes (I) ranging from 1% to 10% by weight in another embodiment.

According to one embodiment of the invention, the composition can comprise at least one wax (Ia) having a melting point of greater than or equal to 70° C. and less than 83° C., at least one wax (Ib) having a melting point ranging from 83° C. to 110° C., as well as mixtures thereof. The composition according to the invention can comprise a mixture of waxes (I) containing at least one first wax (Ia) and at least one second wax (Ib). This mixture of waxes (I) can generally comprise from 5% to 50% by weight of the at least one wax (Ia), relative to the total weight of the said mixture of waxes (I), and from 50% to 95% by weight of the at least one wax (Ib).

Waxes (Ia) which can be useful according to the invention are, for example, rice bran wax and candelilla wax. Waxes (Ib) which can be useful according to the invention are, for example, carnauba wax, ouricury waxes, and montan waxes. Carnauba wax is preferably used.

The composition can also comprise at least one wax (II), referred to as soft wax, having a melting point of greater than or equal to 45° C. and less than 70° C. Wax (II) can have a needle penetration of greater than 7.5 according to one embodiment of the invention, and less than or equal to 217 in another embodiment, measured according to the conditions defined above for the waxes (I). This wax (II) makes it possible to soften the coating applied to the eyelashes.

The waxes (II) which can be useful according to the invention are, for example, beeswax, lanolin waxes, paraffin waxes, cerasin waxes, microcrystalline waxes, ozokerites, spermacetis, certain polyethylene waxes whose molecular weight is such that they satisfy the criteria of the waxes (II), and hydrogenated plant oils.

Among the hydrogenated plant oils which can be useful according to the invention are, for example, hydrogenated jojoba waxes and hydrogenated oils which are obtained by catalytic hydrogenation of fatty substances comprising at least one fatty chain chosen from linear and non-linear $C_8$–$C_{32}$ fatty chains and which have the qualities corresponding to the definition of the waxes. Mention may be made, for example, of hydrogenated sunflower oil, hydrogenated castor oil, hydrogenated cotton oil, hydrogenated coconut oil, and hydrogenated lanolin.

The wax (I) and the wax (II) can be present in the composition in a [wax (I)/wax (II)] weight ratio ranging from 0.2:1 to 1:1 in one embodiment, and ranging from 0.4:1 to 0.7:1 in another embodiment.

The composition can also contain at least one auxiliary film-forming polymer other than the polyurethane polymer defined above, in one embodiment in an amount ranging from 0% to 15% by weight, relative to the total weight of the composition, in another embodiment in an amount ranging from 0.1% to 15% by weight, and in another embodiment in an amount ranging from 0.1% to 10% by weight.

Auxiliary film-forming polymers which can be useful according to the invention are, for example:

cellulose polymers such as hydroxyethylcellulose, hydroxypropylcellulose, hydroxypropylethylcellulose, and ethylhydroxyethylcellulose;

acrylic ester polymers or copolymers, such as polyacrylates and polymethacrylates;

vinyl polymers, such as polyvinylpyrrolidones, copolymers derived from (i) vinylpyrrolidone and (ii) vinyl acetate, and polyvinyl alcohol;

polyesters, polyamides, and epoxyester resins; and polymers of natural origin which are optionally modified, such as gum arabics, guar gum, xanthan derivatives, and karaya gum.

The composition used in the process according to the invention can be in the form of a wax-in-water, water-in-wax, oil-in-water, or water-in-oil dispersion. The water content in the composition in one embodiment can generally range from 1% to 95% by weight, relative to the total weight of the composition, and in another embodiment can range from 10% to 80% by weight.

The composition according to the invention can also comprise at least one volatile oil. The expression "volatile oil" means an oil which is capable of evaporating at room temperature from a support onto which it has been applied; in other words an oil which has measurable vapour pressure at room temperature.

Oils which can be useful according to the invention are, for example, one or more oils that are volatile at room temperature and atmospheric pressure, having, in one embodiment, for example, a vapour pressure, at ambient pressure and temperature >0 mmHg (0 Pa), and a vapour pressure, at ambient pressure and temperature ranging from $10^{-3}$ to 300 mmHg (0.13 Pa to 40,000 Pa) in another embodiment, on condition that the boiling point is greater than 30° C. These volatile oils are favorable for obtaining a film with total "transfer-resistance" properties, i.e., good staying power, such that the composition transfers little or not at all. These volatile oils also make it easier to apply the composition to the skin, mucous membranes, and superficial body growths. These oils can be chosen from, for example, hydrocarbon-based oils, silicone oils, fluoro oils, and mixtures thereof.

The expression "hydrocarbon-based oil" means an oil mainly containing hydrogen and carbon atoms, and possibly oxygen, nitrogen, sulphur, or phosphorus atoms. The volatile hydrocarbon-based oils which can be suitable for the composition according to the invention are, for example, hydrocarbon-based oils containing from 8 to 16 carbon atoms, and, for example, $C_8$–$C_{16}$ isoalkanes (or isoparaffins) and branched $C_8$–$C_{16}$ esters, such as isododecane (2,2,4,4, 6-pentamethylheptane), isodecane, isohexadecane, isohexyl neopentanoate, and mixtures thereof. Other volatile hydrocarbon-based oils such as, for example, petroleum distillates such as those sold under the name Shell Solt by the company Shell can also be used.

Volatile oils which can also be used also include volatile silicones, such as, for example, cyclic volatile silicones, for example those having a viscosity $\leq 8$ centistokes ($8 \times 10^{-6}$ m$^2$/s), such as, for example, octamethylcyclotetrasiloxane, decamethylcyclopentasiloxane, and hexadecamethylcyclohexasiloxane, and volatile linear silicones such as, for example, octamethyltrisiloxane, heptamethylhexyltrisiloxane, heptamethyloctyltrisiloxane, and decamethyltetrasiloxane. Volatile fluoro oils such as, for example, nonafluoromethoxybutane and perfluoromethylcyclopentane may also be used.

The volatile oil can be present in the composition according to the invention in one embodiment in an amount generally ranging up to 80% by weight, relative to the total weight of the composition, ranging from 1% to 80% by weight in another embodiment, ranging up to 65% by weight in another embodiment, and ranging from 1% to 65% by weight in yet another embodiment.

The composition can also comprise at least one non-volatile oil chosen from, for example, non-volatile hydrocarbon-based oils, silicone oils, and fluoro oils.

Non-volatile hydrocarbon-based oils which can be useful according to the invention are, for example:

hydrocarbon-based oils of animal origin, such as, for example, perhydrosqualene;

hydrocarbon-based oils of plant origin, such as, for example, liquid triglycerides of fatty acids of 4 to 10 carbon atoms, such as heptanoic or octanoic acid triglycerides, sunflower oil, grapeseed oil, sesame oil, corn oil, apricot oil, castor oil, avocado oil, olive oil, cereal germ oil, soybean oil, sweet almond oil, palm oil, rapeseed oil, cotton oil, hazelnut oil, macadamia oil, jojoba oil, caprylic/capric acid triglycerides such as those sold by the company Stearineries Dubois or those sold under the names Miglyol 810, 812, and 818 by the company Dynamit Nobel, and liquid karite butter;

linear or branched hydrocarbons of mineral or synthetic origin, such as, for example, petroleum jelly, polydecenes, and hydrogenated polyisobutene such as parleam;

synthetic esters and ethers, such as, for example, the oils of formula $R_1COOR_2$ in which $R_1$ represents a higher fatty acid residue containing from 6 to 29 carbon atoms and $R_2$ represents a hydrocarbon-based chain containing from 3 to 30 carbon atoms, such as, for example, purcellin oil, isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate; polyol esters such as propylene glycol dioctanoate, neopentyl glycol diheptanoate, diethylene glycol diisonanoate, and pentaerythritol esters;

fatty alcohols that are liquid at room temperature and which contain a branched and/or unsaturated carbon-based chain containing from 12 to 26 carbon atoms, such as, for example, octyldodecanol, isostearyl alcohol, oleyl alcohol, 2-hexyldecanol, 2-butyloctanol, and 2-undecylpentadecanol; and higher fatty acids such as myristic acid, palmitic acid, stearic acid, behenic acid, oleic acid, linoleic acid, linolenic acid, and isostearic acid; and mixtures thereof.

The non-volatile silicone oils useful according to the invention can be oils of low viscosity, such as, for example, linear polysiloxanes whose degree of polymerization is from approximately 6 to approximately 2000. Mention may be made, for example, of polydimethylsiloxanes (PDMSs) with a viscosity of greater than 10 mpa·s, phenyl dimethicones, phenyl trimethicones, and polyphenylmethylsiloxanes.

The non-volatile fluoro oils which can be useful in the composition according to the invention can be, for example, fluorosilicone oils, fluoro polyethers, and fluoro silicones as described in document EP-A-847 752, the disclosure of which is incorporated by reference herein.

The non-volatile oils can be present in the composition according to the invention in one embodiment in an amount generally ranging up to 50% by weight, relative to the total weight of the composition, ranging from 0.1 to 50% by weight in another embodiment, ranging up to 20% by weight in another embodiment, and ranging from 0.1% to 20% by weight in yet another embodiment.

The composition according to the invention can contain at least one emulsifying surfactant which is present, for example, in one embodiment of the invention in a proportion ranging from 2% to 30% by weight, relative to the total weight of the composition, and ranging from 5% to 15% by weight in another embodiment. These surfactants can be chosen from anionic and nonionic surfactants. Reference may be made to the document "Encyclopedia of Chemical Technology, Kirk-Othmer", volume 22, pp. 333–432, 3rd edition, 1979, Wiley, for the definition of the properties and the functions (emulsifying) of the surfactants, and particularly pp. 347–377 of that reference for the anionic and nonionic surfactants. These pages from this document are incorporated by reference.

The surfactants which can be used in the composition according to the invention are, for example:

nonionic surfactants, such as, for example, fatty acids, fatty alcohols and polyethoxylated or polyglycerolated fatty alcohols such as polyethoxylated stearyl or cetyl-stearyl alcohol, fatty acid esters of sucrose, alkyl glucose esters, for example, polyoxyethylenated fatty esters of a $C_1$–$C_6$ alkyl glucose; and anionic surfactants, such as, for example, $C_{16}$–$C_{30}$ fatty acids neutralized with amines, aqueous ammonia, or alkaline salts.

For example, surfactants which make it possible to obtain oil-in-water or wax-in-water emulsions can be used.

The composition can also comprise at least one dyestuff such as pulverulent compounds, which can be present, for example, in a proportion ranging from 0.01 to 25% relative to the total weight of the composition. The pulverulent compounds can be chosen from the pigments, nacres, and fillers usually used in mascaras.

The pigments can be chosen from white, colored, mineral, and organic pigments. Among the mineral pigments which may be mentioned are, for example, titanium dioxide, which can optionally be surface-treated, zirconium oxide, cerium oxide, iron oxide, chromium oxide, manganese violet, ultramarine blue, chromium hydrate, and ferric blue. Among the organic pigments which may be mentioned are carbon black, pigments of D & C type and lakes based on cochineal carmine, barium, strontium, calcium, and aluminium.

The nacreous pigments can be chosen from white nacreous pigments, such as, for example, mica coated with titanium or with bismuth oxychloride, and coloured nacreous pigments such as, for example, titanium mica with iron oxides, titanium mica with ferric blue or chromium oxide, titanium mica with an organic pigment of the abovementioned type, as well as nacreous pigments based on bismuth oxychloride.

The fillers can be chosen from those which are well known to a person skilled in the art, and which are commonly used in cosmetic compositions. Fillers which can be used are, for example:

talc, which is a hydrated magnesium silicate used in the form of particles generally less than 40 microns, micas, which are aluminosilicates of varied compositions in the form of flakes having sizes of, for example, from 2 to 200 microns in one embodiment, and from 5 to 70 microns in another embodiment, and a thickness ranging from 0.1 to 5 microns in one embodiment, and ranging from 0.2 to 3 microns in another embodiment, it being possible for these micas to be of natural origin such as muscovite, margarite, roscoelite, lipidolite or biotite, or of synthetic origin;

starch, for example, rice starch;

kaolin, which is a hydrated aluminium silicate in the form of particles of isotropic form which are generally less than 30 microns in size;

zinc oxide and titanium oxide, generally used in the form of particles not exceeding a few microns in size;

calcium carbonate, magnesium carbonate, and magnesium hydrocarbonate;

microcrystalline cellulose;

silica; and powders of synthetic polymers such as polyethylene, polyesters (polyethylene isophthalate or terephthalate), polyamides, such as, for example, those sold under the trade name "Nylon" or "Teflon," and silicone powders.

The composition according to the invention can also contain at least one ingredient commonly used in cosmetics, such as, for example, trace elements, softeners, sequestering agents, fragrances, oils, silicones, thickeners, vitamins, proteins, ceramides, plasticizers, cohesion agents, emollients, and preserving agents, as well as acidifying or basifying agents usually used in cosmetics. Needless to say, a person skilled in the art will take care to select this or these optional additional ingredient(s), and/or the amount thereof, such that the advantageous properties of the composition according to the invention are not, or are not substantially, adversely affected by the addition envisaged.

The composition according to the invention can be prepared according to the known methods of the fields under consideration.

The invention is illustrated in greater detail in the non-limiting examples that follow.

EXAMPLE 1

A mascara composition according to the invention (Example 1) and a comparative mascara composition not forming part of the invention (Example 1A), having the composition below, were prepared:

| | |
|---|---|
| Carnauba wax | 2.4 g |
| Beeswax | 3 g |
| Paraffin wax | 9.5 g |
| 2-Amino-2-methyl-1,3-propanediol | 0.8 g |
| Triethanolamine | 2.4 g |
| Stearic acid | 6.6 g |
| Water-soluble nonionic polymers | 1.4 g |
| Film-forming polymer in aqueous dispersion* | 5 g AM |
| Polyamide fibers (0.3 mm long and 0.9 Dtex from the company Paul Bonte) | 1 g |
| Mixture of dimethiconol in cyclopentasiloxane (15/85)(DC 1501 fluid from the company Dow Corning) | 8 g |
| Black pigments | 7 g |
| Preserving agents | qs |
| Water | qs to 100 g |

*Inventive Example 1: polyester-polyurethane sold under the name Avalure UR 405 by the company Goodrich.
*Comparative Example 1A: ethyl acrylate/methyl methacrylate copolymer sold under the name Daitosol 5000 AD by the company Saito.

Each composition was applied to a test piece of hair and, after drying, each test piece was then rubbed with a pad of cotton wool soaked in water, carrying out 10 wipes. It was found that the cotton wool which was rubbed against the mascara of Example 1A was much blacker than the one which was rubbed against the mascara of Example 1. The inventive mascara composition was thus more transfer-resistant and had good staying power when the hair was exposed to water, even when rubbed, than the comparative mascara composition of Example 1A.

EXAMPLE 2

A mascara having the composition below was prepared:

| | |
|---|---|
| Carnauba wax | 2.4 g |
| Beeswax | 3 g |
| Paraffin wax | 9.5 g |
| 2-Amino-2-methyl-1,3-propanediol | 0.8 g |
| Triethanolamine | 2.4 g |
| Stearic acid | 6.6 g |
| Water-soluble nonionic polymers | 1.4 g |
| Polyester-polyurethane as an aqueous dispersion (Avalure UR 405 from Goodrich) | 5 g AM |
| Cellulose fibers (Natural rayon flock fiber RC1BE-N003-M04 by the company Claremont Flock) | 1 g |

-continued

| | |
|---|---|
| Pigments | 6 g |
| Preserving agents | qs |
| Water | qs to 100 g |

This mascara made it possible to obtain a make-up result which showed good resistance to tears and sweat, and had good staying power. It also imparted good lengthening properties to the eyelashes.

EXAMPLE 3

A mascara having the composition below was prepared:

| | |
|---|---|
| Aqueous dispersion of polyester-polyurethane containing 49% solids (Avalure UR-425 from Goodrich) | 35.8 g AM |
| Cellulose fibers (Natural rayon flock fiber RC1BE - N003 - M04 by the company Claremont Flock) | 1 g |
| Hydroxyethylcellulose (Cellosize QP 4400 H from Amerchol) | 1.82 g |
| Fumed silica (Aerosil 200 from Degussa) | 1.82 g |
| Ethanol | 5 g |
| Propylene glycol | 4.05 g |
| Citric acid | 0.15 g |
| Pigments | 4 g |
| Preserving agents | qs |
| Water | qs to 100 g |

This mascara made it possible to obtain a make-up effect which had good staying power over at least a day, and the eyelashes showed good lengthening.

What is claimed is:

1. A process for cosmetically making up or caring for keratin fibers, comprising applying to the keratin fibers a composition comprising, in a physiologically acceptable medium, fibers and at least one film-forming polymer in the form of particles in aqueous dispersion, wherein the at least one film-forming polymer is chosen from polyurethanes.

2. A process according to claim 1, wherein the polyurethanes are chosen from polyester-polyurethanes and polyether-polyurethanes.

3. A process according to claim 1, wherein the polyurethanes are anionic.

4. A process according to claim 1, wherein the polyurethanes are capable of forming a film which has a hardness ranging from 10 seconds to 200 seconds.

5. A process according to claim 1, wherein the at least one film-forming polymer is present in an amount ranging from 1% to 60% by weight of solids, relative to the total weight of the composition.

6. A process according to claim 5, wherein the at least one film-forming polymer is present in an amount ranging from 2% to 25% by weight of solids, relative to the total weight of the composition.

7. A process according to claim 1, wherein the fibers are chosen from silk fibers, cotton fibers, wool fibers, flax fibers, cellulose fibers, polyamide fibers, viscose fibers, acetate fibers, poly(p-phenyleneterephthalamide) fibers, acrylic polymer fibers, polyolefin fibers, silica fibers, carbon fibers, polytetrafluoroethylene fibers, insoluble collagen fibers, polyester fibers, polyvinyl chloride fibers, polyvinylidene chloride fibers, polyvinyl alcohol fibers, polyacrylonitrile fibers, chitosan fibers, polyurethane fibers, polyethylene phthalate fibers, fibers formed from mixtures of these polymers, and mixtures thereof.

8. A process according to claim 1, wherein the fibers are fibers of synthetic origin.

9. A process according to claim 1, wherein the fibers have a length ranging from 0.1 mm to 10 mm.

10. A process according to claim 9 wherein the fibers have a length ranging from 1 mm to 5 mm.

11. A process according to claim 1, wherein the fibers have a circular or polygonal cross section.

12. A process according to claim 1, wherein the fibers have a cross section which is included in a circle of diameter ranging from 500 nm to 500 μm.

13. A process according to claim 1, wherein the fibers are present in an amount ranging from 0.1% to 10% by weight, relative to the total weight of the composition.

14. A process according to claim 13 wherein the fibers are present in an amount ranging from 0.3% to 5% by weight, relative to the total weight of the composition.

15. A process according to claim 1, wherein the composition further comprises at least one wax.

16. A process according to claim 15 wherein the at least one wax is present in an amount ranging from 0.5% to 40% by weight, relative to the total weight of the composition.

17. A process according to claim 16, wherein the at least one wax is present in an amount ranging from 5% to 30% by weight, relative to the total weight of the composition.

18. A process according to claim 17, wherein the at least one wax is present in an amount ranging from 10% to 25% by weight, relative to the total weight of the composition.

19. A process according to claim 15, wherein the at least one wax is chosen from waxes (I) having a melting point ranging from 70° C. to 110° C.

20. A process according to claim 19, wherein the at least one wax (I) is present in an amount ranging from 0.1% to 20% by weight, relative to the total weight of the composition.

21. A process according to claim 15, wherein the at least one wax is chosen from waxes (II) having a melting point of greater than or equal to 45° C. and less than 70° C.

22. A process according to claim 15, wherein the at least one wax comprises a mixture of waxes (I) having a melting point ranging from 70° C. to 110° C. and waxes (II) having a melting point of greater than or equal to 45° C. and less than 70° C.

23. A process according to claim 22, wherein the at least one wax (II) is present in a [wax (I)/wax (II)] weight ratio ranging from 0.2:1 to 1:1.

24. A process according to claim 1, wherein the composition also comprises at least one auxiliary film-forming polymer in addition to the at least one film-forming polymer.

25. A process according to claim 24, wherein the at least one auxiliary film-forming polymer is present in an amount ranging up to 15% by weight, relative to the total weight of the composition.

26. A process according to claim 1, wherein the composition further comprises water.

27. A process according to claim 26, wherein the water is present in an amount ranging from 1% to 95% by weight, relative to the total weight of the composition.

28. A process according to claim 27, wherein the water is present in an amount ranging from 10% to 80% by weight, relative to the total weight of the composition.

29. A process according to claim 1, wherein the composition further comprises at least one volatile oil.

30. A process according to claim 29, wherein the at least one volatile oils is present in an amount ranging up to 80% by weight, relative to the total weight of the composition.

31. A process according to claim 1, wherein the composition further comprises at least one non-volatile oil.

32. A process according to claim 31, wherein the at least one non-volatile oil is present in an amount ranging up to 50% by weight, relative to the total weight of the composition.

33. A process according to claim 1, wherein the composition further comprises at least one emulsifying surfactant.

34. A process according to claim 33, wherein the at least one emulsifying surfactant is present in an amount ranging from 2% to 30% by weight, relative to the total weight of the composition.

35. A process according to claim 1, wherein the composition further comprises at least one additive chosen from vitamins, trace elements, softeners, sequestering agents, fragrances, oils, vitamins, thickeners, proteins, ceramides, plasticizers, cohesion agents, acidifying or basifying agents, fillers, pigments, emollients, and preserving agents.

36. A process according to claim 1, wherein the composition is in the form of a wax-in-water, water-in-wax, oil-in-water, or water-in-oil emulsion.

37. A cosmetic composition comprising, in a physiologically acceptable medium, fibers, at least one film-forming polymer in the form of particles in aqueous dispersion, wherein the at least one film-forming polymer is chosen from polyurethanes, and at least one wax.

38. A cosmetic composition according to claim 37, wherein the polyurethanes are chosen from polyester-polyurethanes and polyether-polyurethanes.

39. A cosmetic composition according to claim 37, wherein the polyurethanes are anionic.

40. A cosmetic composition according to claim 37, wherein the polyurethanes are capable of forming a film which has a hardness ranging from 10 seconds to 200 seconds.

41. A cosmetic composition according to claim 37, wherein the at least one film-forming polymer is present in an amount ranging from 1% to 60% by weight of solids, relative to the total weight of the composition.

42. A cosmetic composition according to claim 41 wherein the at least one film-forming polymer is present in an amount ranging from 2% to 25% by weight of solids, relative to the total weight of the composition.

43. A cosmetic composition according to claim 37, wherein the fibers are chosen from silk fibers, cotton fibers, wool fibers, flax fibers, cellulose fibers, polyamide fibers, viscose fibers, acetate fibers, poly(p-phenyleneterephthalamide) fibers, acrylic polymer fibers, polyolefin fibers, silica fibers, carbon fibers, polytetrafluoroethylene fibers, insoluble collagen fibers, polyester fibers, polyvinyl chloride fibers, polyvinylidene chloride fibers, polyvinyl alcohol fibers, polyacrylonitrile fibers, chitosan fibers, polyurethane fibers, polyethylene phthalate fibers, fibers formed from mixtures of these polymers, and mixtures thereof.

44. A cosmetic composition according to claim 37, wherein the fibers are fibers of synthetic origin.

45. A cosmetic composition according to claim 37, wherein the fibers have a length ranging from 0.1 mm to 10 mm.

46. A cosmetic composition according to claim 45, wherein the fibers have a length ranging from 1 mm to 5 mm.

47. A cosmetic composition according to claim 37, wherein the fibers have a circular or polygonal cross section.

48. A cosmetic composition according to claim 37, wherein the fibers have a cross section which is included in a circle of diameter ranging from 500 nm to 500 μm.

49. A cosmetic composition according to claim 37, wherein the fibers are present in an amount ranging from 0.1% to 10% by weight, relative to the total weight of the composition.

50. A cosmetic composition according to claim 37, wherein the fibers are present in an amount ranging from 0.3% to 5% by weight, relative to the total weight of the composition.

51. A cosmetic composition according to claim 37, wherein the at least one wax is present in an amount ranging from 0.5% to 40% by weight, relative to the total weight of the composition.

52. A cosmetic composition according to claim 51, wherein the at least one wax is present in an amount ranging from 5% to 30% by weight, relative to the total weight of the composition.

53. A cosmetic composition according to claim 52, wherein the at least one wax is present in an amount ranging from 10% to 25% by weight, relative to the total weight of the composition.

54. A cosmetic composition according to claim 37, wherein the at least one wax is chosen from waxes (I) having a melting point ranging from 70° C. to 110° C.

55. A cosmetic composition according to claim 54, wherein the at least one wax (I) is present in an amount ranging from 0.1% to 20% by weight, relative to the total weight of the composition.

56. A cosmetic composition according to claim 37, wherein the at least one wax is chosen from waxes (II) having a melting point of greater than or equal to 45° C. and less than 70° C.

57. A cosmetic composition according to claim 37, wherein the at least one wax comprises a mixture of waxes (I) having a melting point ranging from 70° C. to 110° C. and waxes (II) having a melting point of greater than or equal to 45° C. and less than 70° C.

58. A cosmetic composition according to claim 57, wherein the at least one wax (II) is present in a [wax (I)/wax (II)] weight ratio ranging from 0.2:1 to 1:1.

59. A cosmetic composition according to claim 37, wherein the composition further comprises at least one auxiliary film-forming polymer in addition to the at least one film-forming polymer.

60. A cosmetic composition according to claim 59, wherein the at least one auxiliary film-forming polymer is present in an amount ranging up to 15% by weight, relative to the total weight of the composition.

61. A cosmetic composition according to claim 37, wherein the composition further comprises water.

62. A cosmetic composition according to claim 61, wherein the water is present in an amount ranging from 1% to 95% by weight, relative to the total weight of the composition.

63. A cosmetic composition according to claim 62, wherein the water is present in an amount ranging from 10% to 80% by weight, relative to the total weight of the composition.

64. A cosmetic composition according to claim 37, wherein the composition further comprises at least one volatile oil.

65. A cosmetic composition according to claim 64, wherein the at least one volatile oil is present in an amount ranging up to 80% by weight, relative to the weight of the composition.

66. A cosmetic composition according to claim 37, wherein the composition further comprises at least one non-volatile oil.

67. A cosmetic composition according to claim 66, wherein the at least one non-volatile oil is present in an amount ranging up to 50% by weight, relative to the total weight of the composition.

68. A cosmetic composition according to claim 37, wherein the composition further comprises at least one emulsifying surfactant.

69. A cosmetic composition according to claim 68, wherein the at least one emulsifying surfactant is present in an amount ranging from 2% to 30% by weight, relative to the total weight of the composition.

70. A cosmetic composition according to claim 37, wherein the composition further comprises at least one additive chosen from vitamins, trace elements, softeners, sequestering agents, fragrances, oils, vitamins, thickeners, proteins, ceramides, plasticizers, cohesion agents, acidifying or basifying agents, fillers, pigments, emollients, and preserving agents.

71. A cosmetic composition according to claim 37, wherein the composition is in the form of a wax-in-water, water-in-wax, oil-in-water or water-in-oil emulsion.

72. A cosmetic composition according to claim 37, wherein the composition is a make-up composition or a cosmetic care composition for keratin fibers.

73. A process for forming a film on keratin fibers, wherein the film is resistant to at least one of water, tears, and perspiration, comprising applying to the keratin fibers a cosmetic composition comprising fibers and at least one film-forming polyurethane polymer in the form of particles in aqueous dispersion.

* * * * *